United States Patent
Pelssers et al.

(10) Patent No.: US 11,433,394 B2
(45) Date of Patent: Sep. 6, 2022

(54) FLOW CONTROL DEVICE (71) Applicant: KONINKLIJKE PHILIPS N.V., Eindhoven (NL)

(72) Inventors: Eduard Gerard Marie Pelssers, Panningen (NL); Herbert Lifka, Eindhoven (NL); Roland Alexander Van De Molengraaf, Geldrop (NL); Daan Anton Van Den Ende, Breda (NL); Franciscus Johannes Gerardus Hakkens, Eersel (NL); Mark Thomas Johnson, Arendonk (BE); Cornelis Petrus Hendriks, Eindhoven (NL); Anja Van De Stolpe, Vught (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 709 days.

(21) Appl. No.: 16/467,077

(22) PCT Filed: Dec. 11, 2017

(86) PCT No.: PCT/EP2017/082195
§ 371 (c)(1),
(2) Date: Jun. 6, 2019

(87) PCT Pub. No.: WO2018/108799
PCT Pub. Date: Jun. 21, 2018

(65) Prior Publication Data
US 2019/0383281 A1    Dec. 19, 2019

(30) Foreign Application Priority Data
Dec. 13, 2016 (EP) .................................... 16203587

(51) Int. Cl.
*B01L 3/00*    (2006.01)
*A61M 5/142*    (2006.01)
(Continued)

(52) U.S. Cl.
CPC ... *B01L 3/502738* (2013.01); *A61M 5/14276* (2013.01); *B01F 25/311* (2022.01);
(Continued)

(58) Field of Classification Search
CPC ....... B01L 3/502738; B01L 2300/0816; B01L 2300/0867; B01L 2300/0887;
(Continued)

(56) References Cited

U.S. PATENT DOCUMENTS 5,364,602 A    11/1994 Leduc
6,314,317 B1    11/2001 Willis et al.
(Continued)

FOREIGN PATENT DOCUMENTS

| CN | 102159863 A | 8/2011 |
| CN | 202843784 U | 4/2013 |

(Continued)

OTHER PUBLICATIONS

International Search Report dated Jun. 11, 2019.
(Continued)

*Primary Examiner* — Jennifer Wecker
*Assistant Examiner* — Oyeleye Alexander Alabi
(74) *Attorney, Agent, or Firm* — Schott, P.C.

(57) ABSTRACT

A flow control device comprises a laminate structure of an electroactive material layer and a non-actuatable layer. An array of orifices is formed in one of the layers wherein the orifices are open in one of the rest state and actuated state and the orifices are closed in the other of the rest state and actuated state. Actuation of the electroactive material layer causes orifices to open and close so that flow control function may be implemented.

16 Claims, 6 Drawing Sheets

(51) Int. Cl.
  *F04B 43/04* (2006.01)
  *F04B 53/10* (2006.01)
  *F16K 99/00* (2006.01)
  *B01F 25/31* (2022.01)
  *B01F 25/316* (2022.01)
  *B01F 33/30* (2022.01)
  *A61M 25/00* (2006.01)

(52) U.S. Cl.
  CPC ............ *B01F 25/316* (2022.01); *B01F 33/30* (2022.01); *F04B 43/043* (2013.01); *F04B 53/1067* (2013.01); *F16K 99/0025* (2013.01); *F16K 99/0049* (2013.01); *A61M 2025/0058* (2013.01); *B01L 2300/0816* (2013.01); *B01L 2300/0867* (2013.01); *B01L 2300/0887* (2013.01); *B01L 2300/12* (2013.01); *B01L 2400/0633* (2013.01); *B01L 2400/082* (2013.01); *F16K 2099/0076* (2013.01); *F16K 2099/0084* (2013.01); *F16K 2099/0088* (2013.01)

(58) Field of Classification Search
  CPC ......... B01L 2300/12; B01L 2400/0633; B01L 2400/082; A61M 5/14276; A61M 2025/0058; B01F 25/311; B01F 25/316; B01F 33/30; F04B 43/043; F04B 53/1067; F16K 99/0025; F16K 99/0049; F16K 2099/0076; F16K 2099/0084; F16K 2099/0088; F16K 99/0015
  See application file for complete search history.

(56) References Cited

U.S. PATENT DOCUMENTS

| | | |
|---|---|---|
| 9,121,526 B2 | 9/2015 | Giridhar |
| 9,155,861 B2 | 10/2015 | Hetke et al. |
| 10,188,761 B2 | 1/2019 | Tan et al. |
| 2012/0078188 A1 | 3/2012 | Hetke et al. |
| 2013/0144223 A1 | 6/2013 | Hewitt et al. |
| 2013/0207510 A1 | 8/2013 | Poole |
| 2015/0319514 A1 | 11/2015 | Hitchcock et al. |

FOREIGN PATENT DOCUMENTS

| | | | |
|---|---|---|---|
| CN | 104471446 A | 3/2015 | |
| JP | 2002-513318 A | 5/2002 | |
| JP | 2005-522162 A | 7/2005 | |
| WO | 9622795 A1 | 8/1996 | |
| WO | 2009096822 A1 | 8/2009 | |
| WO | WO-2009096822 A1 * | 8/2009 | ........... A61K 9/0009 |
| WO | 20170216086 A1 | 12/2017 | |
| WO | 2018046078 A1 | 3/2018 | |

OTHER PUBLICATIONS

Pelrine et al. "Applications of Dielectric Elastomer Actuators" Visual Communications and Image Processing Jan. 20, 2004, vol. 4329, p. 335-349.

Fang et al. "A Novel Diaphragm Micropump Actuated By Conjugated Polymer Petals" Sensors and Actuators, A 158 (2010) p. 121-131.

* cited by examiner

FLOW CONTROL DEVICE

CROSS-REFERENCE TO PRIOR APPLICATIONS

This application is the U.S. National Phase application under 35 U.S.C. §371 of International Application No. PCT/EP2017/082195, filed on Dec. 11, 2017, which claims the benefit of EP Patent Application No. EP 16203587.7, filed on Dec. 13, 2016. These applications are hereby incorporated by reference herein.

FIELD OF THE INVENTION

This invention relates to a fluid control device, in particular for transport of small doses of fluid.

BACKGROUND OF THE INVENTION

Accurate small dose control is critical in many areas such as medicine and fluid and gas delivery.

In healthcare, there is a trend towards the development of so-called Point Of Care (POC) devices, which are small devices, often with disposable components such as cartridges, that can be used in diagnosis and treatment of patients as an alternative to large and expensive analysis equipment.

Such devices may be used to perform diagnostic tests for example to measure the cellular composition of blood, as well as to enable control of the delivery of small doses of medicine.

Several solutions for in-body medicine dose control have been proposed. One example is the so-called intelligent pill, of Medimetrics (trade mark). This allows individual dose-adjusted delivery to targeted areas of the gastrointestinal tract. The drug delivery is for example performed based on pH sensing, and the operation of a miniature motor to move a plunger.

Another example is a lab on a chip device which provides localized microfluidic drug delivery.

US 2012/0078188 discloses a drug delivery system for in-body drug delivery in which fluidic threads are implanted into tissue. The threads have fluid delivery ports which are operated as controllable valves. The ports are formed as a metal mesh over which an electroactive polymer coating is provided. Actuation of the electroactive polymer coating closes the openings between the mesh wires.

The known devices are generally complicated and they are not able to provide accurate control of the doses within the body. There are similar difficulties in controlling low flow rates.

There are also difficulties performing a sampling process within a miniaturized device. For example, it would be desirable to be able to sample periodically a fluid without saturating a sensor.

It is noted that dose control, flow control and sampling are of interest for liquids and gases. Furthermore, dose control, flow control and sampling in the microliter range are of interest for medical as well as non-medical applications.

It would therefore be desirable to have a reliable flow control device for fluid delivery or sampling, with a simple design which is able to be miniaturized.

SUMMARY OF THE INVENTION

The invention is defined by the claims.

According to examples in accordance with an aspect of the invention, there is provided a flow control device comprising:

a laminate structure of an electroactive material layer having a rest state and an actuated state, and a non-actuatable layer, the electroactive material layer comprising a planar layer when in one of the actuated state and rest state with opposing parallel surfaces, and the non-actuatable layer being provided on one of the surfaces;

an array of orifices formed either in the electroactive material layer thereby defining a perforated planar electroactive material layer or else formed in the non-actuatable layer, wherein the orifices are open in one of the rest state and actuated state and the orifices are closed in the other of the rest state and actuated state;

an electrode arrangement comprising two solid state electrodes in contact with the electroactive material layer on the parallel surfaces for driving the electroactive material layer between the rest state and the actuated state; and a controller for controlling actuation of the electroactive material layer.

This design provides a laminate structure which is easy to produce and to miniaturize. Actuation of the electroactive material layer causes the orifices to open and close so that a flow control function may be implemented. The laminate structure comprises at least two layers which are bonded together, and they are preferably planar in a non-actuated state. The two layers comprise a bottom layer and a top layer bonded or otherwise coupled together. The device can be made to provide very accurate control of very small amounts of liquid, at low power and low cost and with silent operation. The device can be miniaturized to a desired scale.

In a first design, the array of orifices is formed in the electroactive material layer, and the non-actuatable layer comprises an array of stiffening elements provided over the electroactive material layer at locations between the orifices. The non-actuatable layer also has openings at the locations of the orifices, so that there is a through passage formed at the orifices.

The stiffening elements mean that the deformation of the electroactive material takes place preferentially at the locations of the orifices, so that they may open and close. In this design, the electroactive material is formed as a perforated membrane.

In a second design, the array of orifices is formed in the non-actuatable layer which comprises a grid of segments, the orifices comprising spaces between the segments of the grid. In this way, the elements of the grid are moved together or apart by the electroactive material layer which carries them as a result of the laminate structure.

In this second design, channels or openings may also be provided in the electroactive material layer. These enable a flow path to be formed between opposite sides of the device.

The orifices may be closed in the rest state. This means the device reverts to a safe valve closed setting in the absence of a control signal.

The device may comprise a sealing layer which is provided at least around the internal openings of the orifices. This sealing layer enables the valve closed function to be improved.

The device may comprise a breakable outer protection layer which is adapted to be broken by first actuation of the device. This provides a protection function before the device is used.

The electroactive material layer may be adapted to expand in-plane or to bend when actuated. A bending function may be used to provide pumping action. For example the device may be used in combination with a container to form a closed system. Flow control and pumping functions can then be combined into one device.

The flow control device may be used in various applications.

A first example is a medicine delivery system comprising:
a reservoir of medicine;
the flow control device as defined above; and
a fluid connection between the reservoir of medicine and the flow control device.

The medicine delivery system may be used for delivering medicine internally to a specific location within the body. The reservoir may be at the location of the flow control device, for example it may be a chamber having an outer wall formed by the flow control device. Alternatively, the reservoir may be more remote from the flow control device, with a fluid connection (e.g. a catheter) between them.

The flow control device may comprise a chamber having a first face formed by the flow control device and a second face formed by a second electroactive material actuator for providing a pumping function. In this way, the delivery may be actively pumped by a second electroactive material actuator. However, the two actuators may share a common actuation signal.

The flow control device may instead comprise a chamber having a first face formed by the flow control device, wherein the electroactive material layer is adapted to bend when actuated for providing a pumping function. In this way, a single actuator may provide both orifice control and pumping.

A second example is a fluid reaction or mixing system comprising:
a set of reservoirs of different fluids;
a respective flow control device as defined above at a fluid output of each reservoir; and
a shared mixing reservoir at the output of the flow control devices.

The different fluids in different reservoirs may be provided to the mixing chamber at different times, to provide a controlled chemical function.

Flow control valves may be provided at an inlet and an outlet of the shared mixing chamber. This enables a closed chamber to be formed within which a reaction may be controlled to take place.

This controlled mixing function may for example find application in a culturing device where a dual biological cell layer is realized by culturing cells on both sides of the flow control device. Such a device may be used in the field of organ on a chip.

A third example is a fluid analysis system comprising:
a sensing chamber;
a fluid sensor mounted in the chamber; and
a flow control device as defined above for controlling the flow of fluid into the sensing chamber.

The flow control device performs a sampling function and this may prevent saturation of the fluid sensor.

A fourth example is a fluid filtering system, comprising:
a flow control device as defined above,
wherein the controller is adapted to control the orifice size thereby to provide a tunable particle filtering function.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a flow control device comprising a laminate structure of an electroactive material layer and a non-actuatable layer. An array of orifices is formed in one of the layers wherein the orifices are open in one of the rest state and actuated state and the orifices are closed in the other of the rest state and actuated state. Actuation of the electroactive material layer causes orifices to open and close so that flow control function may be implemented.

The invention makes use of a control device using an electroactive material (EAM). This is a class of materials within the field of electrically responsive materials. When implemented in an actuation device, subjecting an EAM to an electrical drive signal can make them change in size and/or shape. This effect can be used for actuation and sensing purposes.

There exist inorganic and organic EAMs.

A special kind of organic EAMs are electroactive polymers (EAPs). Electroactive polymers (EAP) are an emerging class of electrically responsive materials. EAPs, like EAMs can work as sensors or actuators, but can be more easily manufactured into various shapes allowing easy integration into a large variety of systems. Other advantages of EAPs include low power, small form factor, flexibility, noiseless operation, and accuracy, the possibility of high resolution, fast response times, and cyclic actuation. An EAP device can be used in any application in which a small amount of movement of a component or feature is desired, based on electric actuation. Similarly, the technology can be used for sensing small movements. The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-20 kHz.

Figure 1:
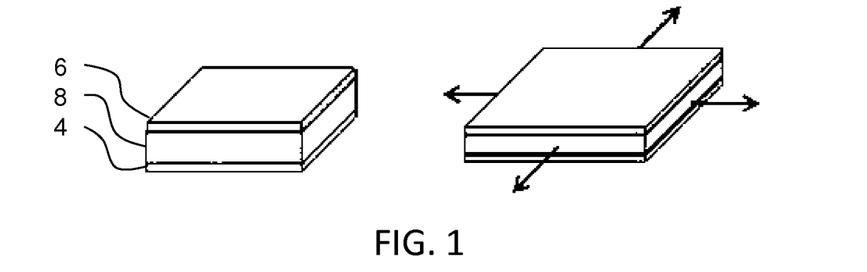
FIG. 1 shows a known electroactive polymer device which is not clamped.
Figure 2:
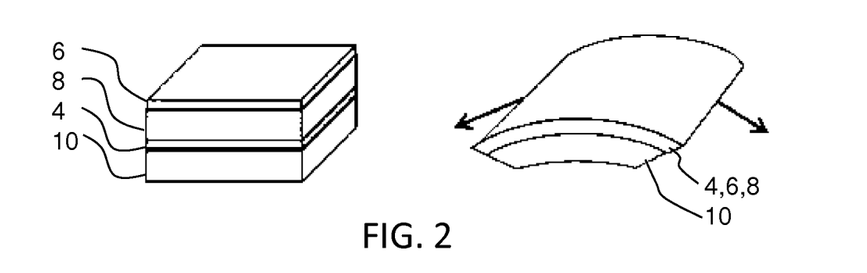
FIG. 2 shows a known electroactive polymer device which is constrained by a backing layer.

As an example of how an EAM device can be constructed and can operate, FIGS. 1 and 2 show two possible operating modes for an EAP device that comprises an electroactive polymer layer 8 sandwiched between electrodes 4, 6 on opposite sides of the electroactive polymer layer 8.

FIG. 1 shows a device which is not clamped to a carrier layer. A voltage is used to cause the electroactive polymer layer to expand in all directions as shown.

FIG. 2 shows a device which is designed so that the expansion arises only in one direction. To this end the structure of FIG. 1 is clamped or attached to a carrier layer 10. A voltage is used to cause the electroactive polymer layer to curve or bow. The nature of this movement arises from the interaction between the active layer which expands when actuated, and the passive carrier layer which does not.

Figure 3:
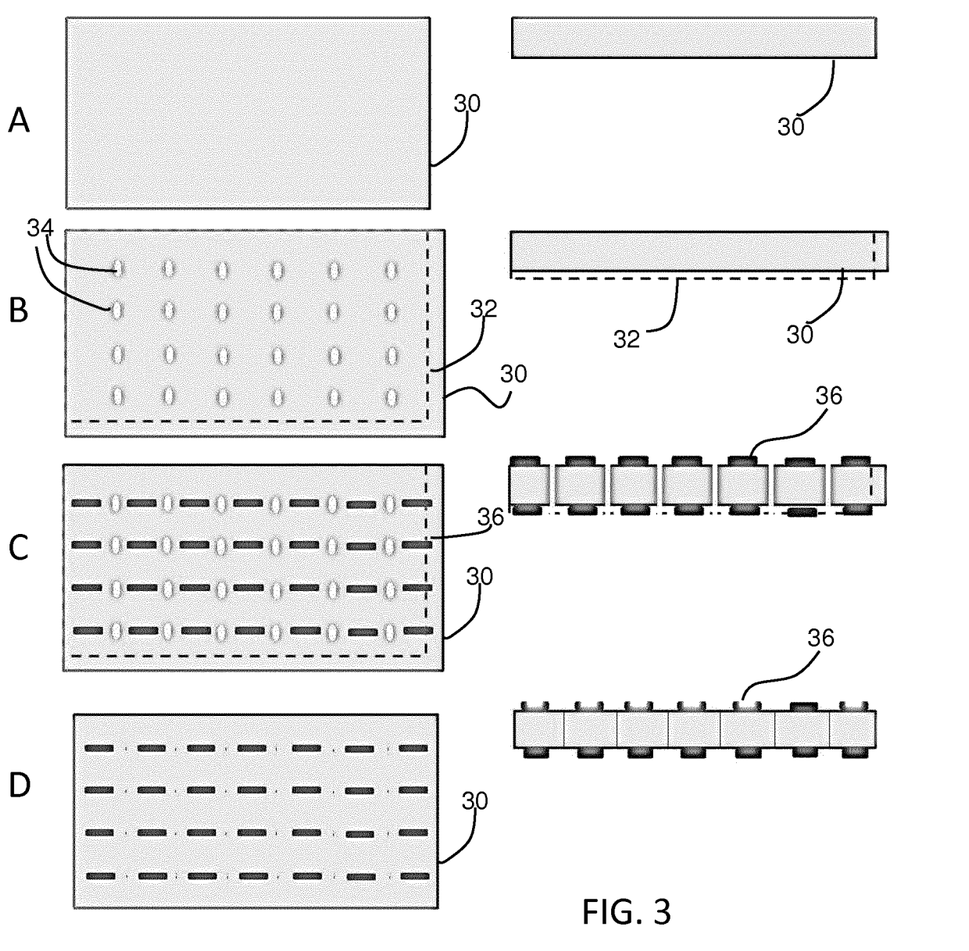
FIG. 3 shows a first example of a flow control device, and shows steps in the manufacture of the device.

FIG. 3 shows a first example of a flow control device, and shows steps in the manufacture of the device.

FIG. 3A shows a planar layer 30 of electroactive material, in particular an electroactive polymer, in a non-actuated state. The plan view is shown to the left and a cross sectional side view is shown to the right. The layer 30 is driven by electrodes which are not shown. There is also a controller (shown schematically as 42 in FIG. 4) for controlling the application of drive signals (i.e. the drive signal level and timing) to the electrodes.

The electrodes comprise first and second solid electrodes in contact with opposite sides of the layer 30. The device can be used in air, and it can be used to control any fluid. The electrodes for example each comprise a sheet electrode formed from elastic conducting material which deforms with the electroactive polymer. There may be openings in the electrode layers either corresponding to the openings, or larger than the openings. The openings may be formed before or after forming the electrodes. Preferable, the opening are formed after the electrodes are formed, so that they are formed on a continuous planar surface, and the electrodes on the two sides remain separate.

In a preferred example, the electrodes are formed as a very thin (and conformable) evaporated metal coating. The full surface of the layer 30 is for example coated. After this, a resist is deposited on the surface and locally illuminated with light through a mask which develops the resist. The developed resist is removed. Then the metal electrode layer is locally removed by etching at the location where the holes are to be formed. The remaining resist is then removed, thus giving a conventional lithography based deposition process.

If the membrane is to be used in a conducting fluid, the electrode layer may be covered with a conformable insulating layer. This can for instance be a sprayed or dipped polymer coating. The coating can be dried and cured after deposition.

The conformable electrode can also be formed by printing a conductive layer on the surface of the electroactive layer 30. The printed material can be a flexible (conformable) polymer-conductive metal particle composite. The electrode can cover the complete surface apart from the holes and surrounding area or can also be a meandering pattern. An insulating polymer can be printed over it if required.

Other options are screen printing or electrolytic processes in combination with local etching. Meandering structures can again be used to support deformation.

A drive voltage is applied to cause the layer 30 to expand in-plane resulting in the increased size shown in FIG. 3B. The original size is shown as the dotted line 32. Furthermore, an array of orifices 34 is formed in the layer for example by laser drilling or cutting. The orifices are generally circular or oval in this example. However, the term "orifice" is intended to have broader meaning, and covers any passageway extending through the layer including stripes and indeed a grid formed by orthogonal stripes (as will become clear further below).

In this example, the electroactive material layer 30 is a perforated layer. By this is meant the layer has a uniform thickness and planar opposing surfaces, but there is a set of orifices extending through the thickness of the layer. Preferably, these orifices are formed as openings through a previously continuous layer. The planar nature of the layer facilities the provision of electrodes on opposing surfaces as mentioned above.

The openings may be provided through the stack of EAP layer and electrode layers, or the electrode layers may be provided as patterned layers after the formation of the perforated layer 30.

A non-actuatable layer is bonded to the electroactive material layer 30. In the example of FIG. 3, this non-actuatable layer comprises an array of stiffening elements 36 provided over the electroactive material layer 30 at locations between the orifices. This is shown in FIG. 3C.

The non-actuatable layer thus may occupy a relatively small fraction of the overall area, in particular less than 50% or even less than 25% of the overall area.

The electroactive material may be a volume changing material or it may be an incompressible material such as a dielectric elastomer. The control may be based on both ionic and field-driven EAPs for example enabling fast actuation speeds if desired (e.g. <1 second).

The non-actuatable layer is deformable so that it follows the deformation of the laminated electroactive material layer. This deformability may be because there are open spaces between discrete isolated elements (and those elements may then be rigid) or it may be because the material of the non-actuatable layer is itself deformable.

The stiffening elements 36 are formed from a material that has a stiffness which is large compared to that of the electroactive material. As the stiffness of the electroactive material strongly depends on the type of material applied (for example ranging from very soft silicones to more stiff ter-polymers), the elements 36 can be made from a wide range of materials. The elements 36 are typically made of a polymer although metals or ceramics are also possible.

Filled polymers (to increase the stiffness) can be applied, with particle or fiber filling. Polyimide (PI) is one example which is stiff and is widely used in electronic devices, and it can for instance be spin coated. Other options include Nylon (PA), polyesters, polyether ketone (PEEK), polyethylene terephthalate (PET), polyethylene (PE) and polycarbonate (PC).

The non-actuatable layer may be an array of separate elements as shown in FIG. 3 or it may be a single patterned layer in the form of a profiled substrate. The non-actuatable layer is also laminated with the electroactive material layer in the actuated state.

The drive voltage is then removed. The electroactive material layer then shrinks to the condition shown in FIG. 3D. The stiffening elements generate a compressive stress around the orifices 34, which closes them.

This design is a normally closed design, with the orifices closed in the rest state of the electroactive material layer and opened in the actuated state. By controlling the actuation voltage the opening size can be controlled.

A normally open design is also possible, with the orifices open in the rest state of the electroactive material layer and closed in the actuated state. For this purpose, the orifices are formed in the rest state and lateral expansion is constrained during actuation by the stiffening elements. As a result, compressive stress will build up which results in closing of the holes.

Figure 4:
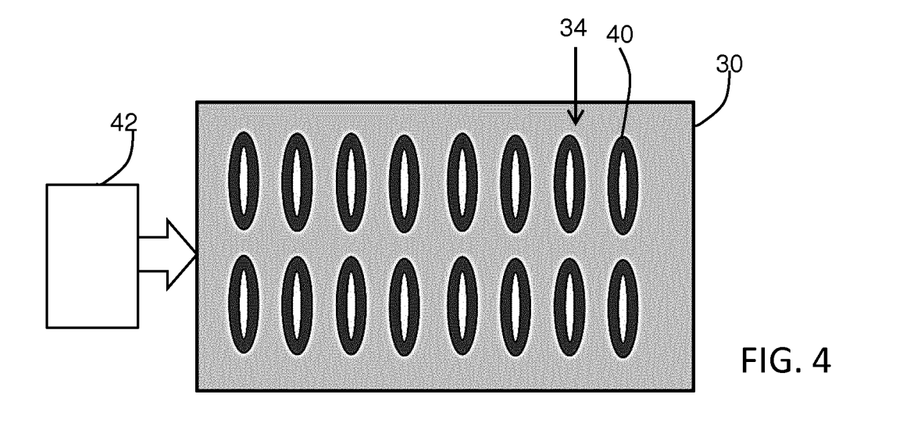
FIG. 4 shows that a sealing layer may be provided at least around the internal openings of the orifices in the device of FIG. 3.

FIG. 4 shows that a sealing layer 40 may be provided at least around the internal openings of the orifices 34. For example, a rubbery material can be added to prevent fluid (e.g. gas or liquid) leakage. The layer 40 may also provide protection to the orifice opening or to the fluid passing through the opening.

The orifices may for example be lined with a dielectric coating to avoid electrical discharge through the gas or liquid flowing through the orifice. This coating can for instance be applied by dipping the layer in a coating liquid and applying air pressure through the device to re-open any fully closed holes if necessary. For better control of the hole diameter, the hole can be re-drilled to the desired size after coating.

It is also possible to seal the device for example with a SiN layer after the laser drilling. This SiN then acts as an environment protection layer and will break at first operation due to expansion of the electroactive material layer.

The flow control device may form an outlet of a fluid chamber, which is controlled to allow fluid to enter the chamber or leave the chamber.

Figure 5:
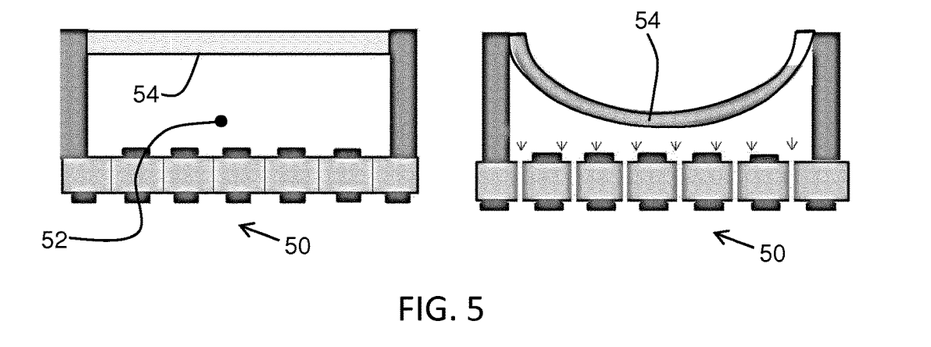
FIG. 5 shows a medicine delivery system comprising a flow control device.

FIG. 5 shows a medicine delivery system comprising a flow control device 50 as described above which forms a surface of a chamber 52. The chamber 52 connects to a reservoir of medicine. This system may be embedded in an intelligent pill.

FIG. 5 also shows an option by which a second electroactive material actuator 54 forms another surface of the chamber 52 for use in pressing the medicine out. The flow control device thus comprises a chamber 52 having a first face formed by the flow control device 50 and a second face formed by the second electroactive material actuator 54. The left image shows the rest state of both the flow control device 50 and the second actuator 54 and the right image shows the actuated state of both the flow control device 50 and the second actuator 54. The same control signal may be used, so that a pumping action starts when a voltage is applied to the second actuator at the same time that the orifices in the flow control device 50 are opened. This simplifies the driving electronics and saves space.

As soon as the activation is stopped, the fluid cannot flow out from the chamber 52. By controlling the voltage, the opening sizes can also be controlled. Therefore the amount of medicine delivered can be controlled.

A number of these medicine delivery elements may be combined on a substrate.

Figure 6:
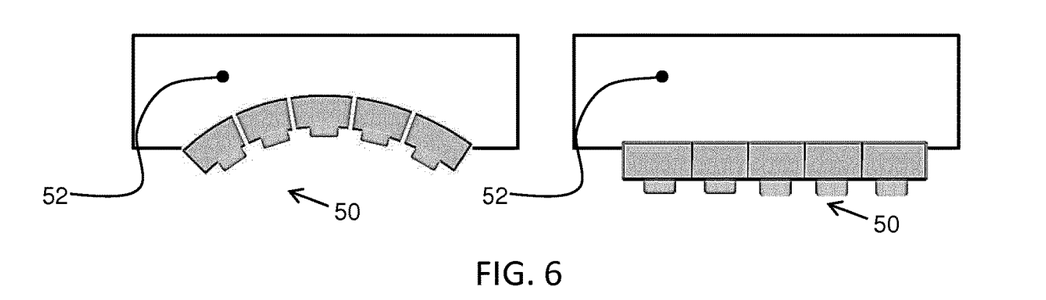
FIG. 6 shows a variation of the concept of FIG. 5 in which the electroactive material layer of the flow control device is adapted to bend when actuated.

FIG. 6 shows a variation of the same concept in which the electroactive material layer of the flow control device 50 is adapted to bend when actuated for providing the pumping function.

To manufacture this variant, the electroactive material actuator is actuated by applying the voltage so that it bends and holes are then drilled in the bent configuration. The actuator straightens when the drive signal is removed, and the holes are then closed. A single voltage controls the bending action as well as orifice size in the device.

By using a single bending actuator that is also the membrane, the functions of pressing and flow control can be combined.

Multiple delivery systems as described above may be combined for example for mixing chemicals or medicines.

Figure 7:
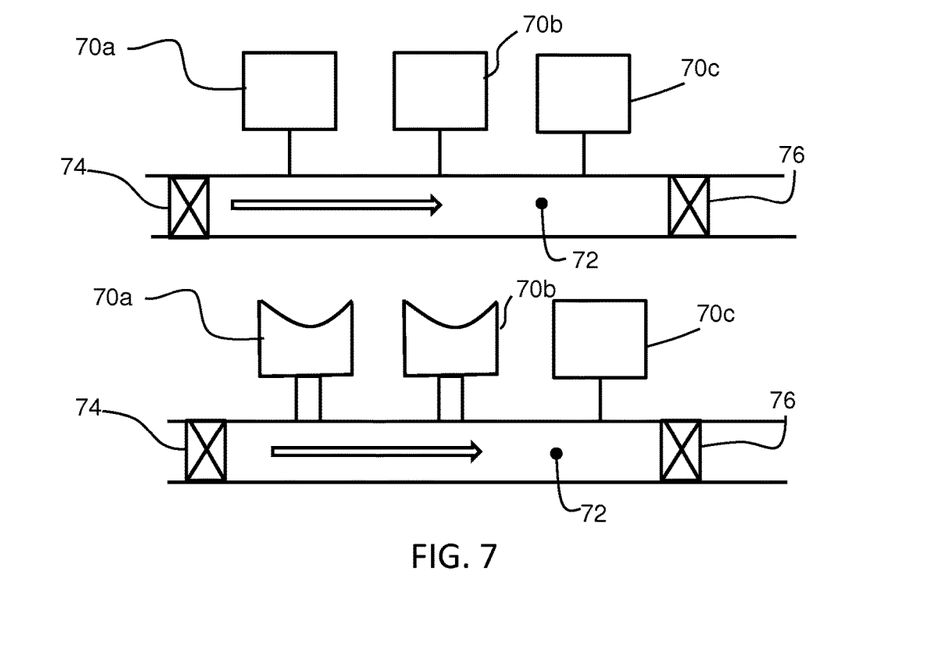
FIG. 7 shows a fluid reaction or mixing system.

FIG. 7 shows a fluid reaction or mixing system. There is a set of reservoirs 70a, 70b, 70c of different fluids. Each reservoir connects to a shared mixing chamber 72 through a respective flow control device as described above. There may also be flow control valves 74, 76 at an inlet and an outlet of the shared mixing chamber 72.

This system allows several different chemicals or medicines to be mixed, and they can be provided in a reaction/mixing chamber for a certain time. Different chemicals can be added in sequence and allowed to react for desired time periods before transporting the end product to another mixing/reaction chamber or to the outside.

This system may be implemented as a lab-on-a-chip or even in a pill which can fabricate the medicines in real time in the body. Many variants and systems are possible by combing the flow control devices with respective storage chambers.

The system of FIG. 7 may be used as a lab-in-a-pill system. With the valves 74, 76 open, blood from the veins flows freely through the mixing chamber 72. The mixing chamber is then closed by activating the valves 74, 76, which may also be implemented as electroactive material valves, for example of the same type as the flow control device as described above. However, a single opening valve may be formed, for example as a MEMs valve device.

By way of example, as shown in the bottom image of FIG. 7, for a defined time the flow control device for chamber 70a is opened and for another time the flow control device for the chamber 70b is opened. This may actively pump fluid into the mixing chamber in the manner explained with reference to FIG. 5.

To improve the mixing, an extra electroactive material actuator may be provided which moves the fluid in the mixing chamber.

There are many possible designs and types of electroactive material actuator suitable for this function. One option is an electroactive material bending actuator integrated in the wall of the mixing chamber. The actuation induces turbulence and promotes fluid movement and mixing within the chamber. A flexible part in the mixing chamber is then provided to accommodate the volume change during actuation. Two bending actuators may be integrated in the wall of the mixing chamber (operated oppositely to maintain a constant volume), or one bending actuator and one flexible membrane may be used.

The flow control device associated with chamber 70c may be opened at a later time. After reacting in the mixing chamber the valves 74, 76 are opened again and the mixture can flow into the blood.

Figure 8:
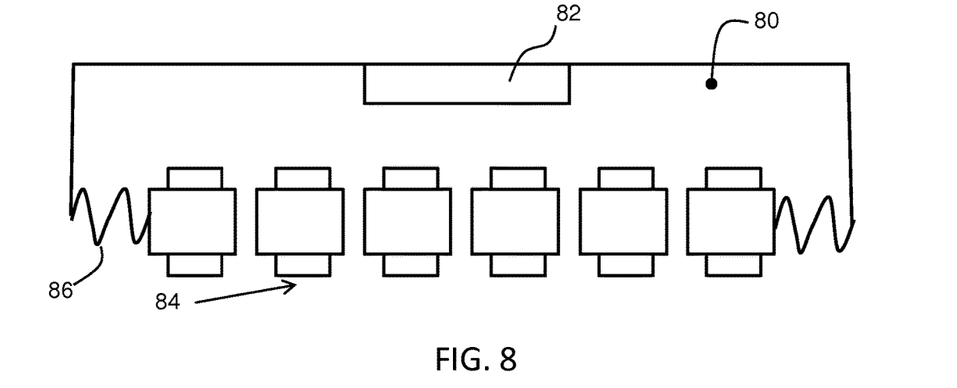
FIG. 8 shows a fluid analysis system.

FIG. 8 shows a fluid analysis system comprising a sensing chamber 80 and a fluid sensor 82 mounted in the chamber. A flow control device 84 as described above controls the flow of fluid into the sensing chamber. The flow control device thus forms a sensing membrane.

The sensing membrane is suspended by springs 86. The sensing membrane enables periodic sampling of fluid (liquid or gas) and therefore avoids saturation of the sensor. The springs fix the membrane in the up-down direction (of FIG. 8) but allow in-plane expansion. FIG. 8 shows the actuated (open pore) state.

The sensing membrane is switchable so that it implements a valve function.

The sensing membrane may also be used as a filter with adaptable orifice (i.e. pore) sizes being capable of filtering different sized fractions of particular matter by adapting the electroactive material drive voltage.

The examples above make use of a perforated electroactive material layer. Other examples make use of a separate layer for providing the orifices, and a continuous or substantially continuous electroactive material layer.

Figure 9:
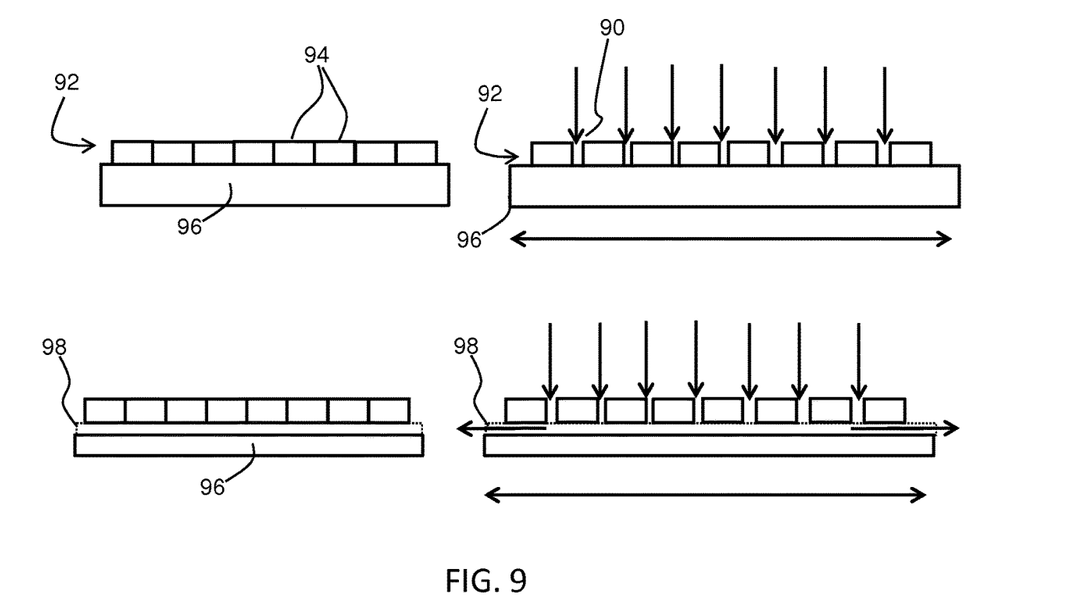
FIG. 9 shows an alternative example of a flow control device.

FIG. 9 shows an example of a flow control device having the array of orifices 90 formed in the non-actuatable layer 92 which comprises a grid of segments 94. The orifices comprise spaces between the segments 94 of the grid.

The electroactive material layer 96 is then a continuous layer.

In the upper left part of FIG. 9, the electroactive material layer 96 is not actuated and the segments 94 are located next to each other. The segments 94 are attached to the electroactive material layer 96 at pinning positions. In the upper right part of the FIG. 9 the electroactive material layer 96 is in the actuated state and the segments 94 are shifted with respect to each other creating slit like orifices 90.

The flow needs to pass through or around the electroactive material layer. For this purpose, channels or openings may be provided in the electroactive material layer or in the grid segments.

The lower part of FIG. 9 shows non-actuated and actuated state of the electroactive material layer at a cross section where a channel 98 runs in the electroactive material layer. This channel enables flow through the orifices. The channels are formed by a locally thinner region of the electroactive material layer, but it may instead be formed by a locally thinner region of the grid segments 94.

The arrangement shown functions as a normally closed valve or membrane but the opposite configuration may instead be used.

Most examples above are based on deflection of the electroactive material layer in-plane. However, the flow control device may instead be design to deform by bending as mentioned above.

Figure 10:
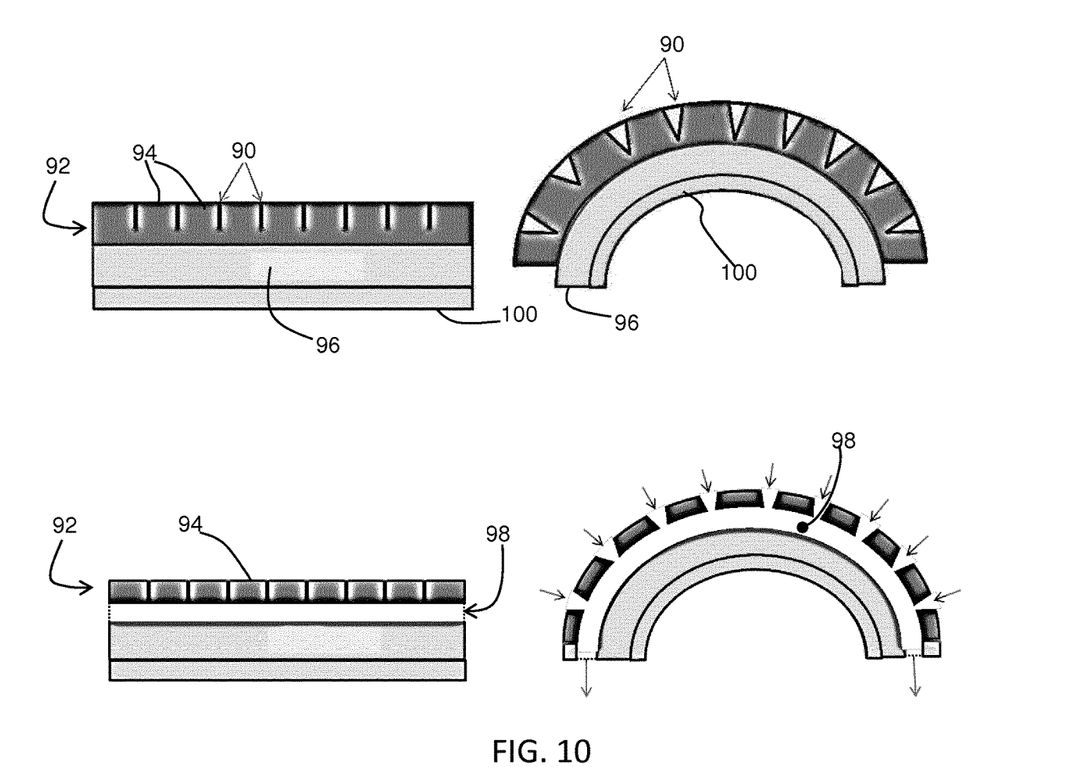
FIG. 10 shows a design similar to FIG. 9, in which the electroactive material layer bends when the device is actuated.

FIG. 10 shows images corresponding to those of FIG. 9, in which the electroactive material layer 96 has a base layer 100 used to create bending when the device is actuated.

The segments 94 are joined together at their base, and the orifices only extend through the non-actuated layer 92 where channels are formed in the non-actuated layer.

When the electroactive material layer 96 is not actuated the segments 94 are located next to each other and minimal fluid can pass. When the electroactive material layer is actuated a bending of the structure will occur since the base layer 100 does not expand. Consequently slit like orifices are induced as shown in the right part of the figure.

For the cross section through a channel 98 of the non-actuated layer it can be seen that orifice openings are formed.

The electroactive material layer and base layer can be provided with holes and in this case channels are not required (but the orifices need to open when the layer is deformed). Alternatively the base layer 100 can be omitted, and the electroactive material layer and its grid elements may be clamped on two sides, which will also induce a bending.

The actuator with membrane can also be clamped (i.e. fixed at both ends) to cause bending. A design which provides a small pre-bend to the shape induces the actuator to bend in the right direction.

Figure 11:
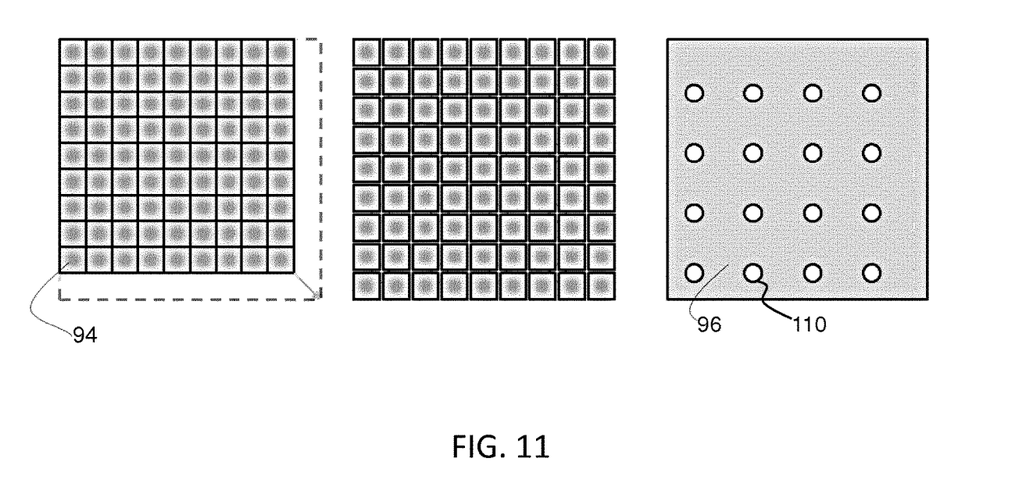
FIG. 11 shows a top view the electroactive material layer with grid elements for the design of FIG. 9.

FIG. 11 shows a top view the electroactive material layer with grid elements for the planar design of FIG. 9. The left image shows the non-actuated state. The middle image shows the actuated state and the right image shows the electroactive material layer 96.

In this example there are no channels but instead holes 110 in the electroactive material layer so that fluid can pass the orifices and can flow through the general plane of the device.

By way of example, the with a linear expansion of 4% and substrate elements of length 500 micrometers, the created slit width during actuation will be 20 micrometers.

The flow control device may for example find application in a culturing device where a dual biological cell layer is realized by culturing cells on both sides of the device. The orifices enable the two cell layers to interact. In particular, for investigations where a gradual change in permeability is desired, an adaptable orifice (i.e. pore) size is beneficial. This may for example mimic permeability changes or increasing stiffness of a blood vessel. As such, one of the cell layers will mimic the endothelium of a blood vessel and the other cell layer will mimic a tissue.

In addition, the orifices may initially be closed, so that a confluent cell layer on each side is created before the two cell layers are allowed to interact via the orifices in an open state. In this way, the cell type of the first layer does not mix with the cell type of the second layer and vice versa.

In addition to gradually adapting the orifice size, a dynamic mechanical deformation of the membrane (stretching) is often an essential function to mimic the natural environment of cells, for instance dynamic tissue deformation in arterial blood vessels (pulsed blood flow), heart (pumping), or lungs (breathing). A small dynamic tissue deformation superimposed on a gradually changing orifice size can be simulated with the same actuator.

Figure 12:
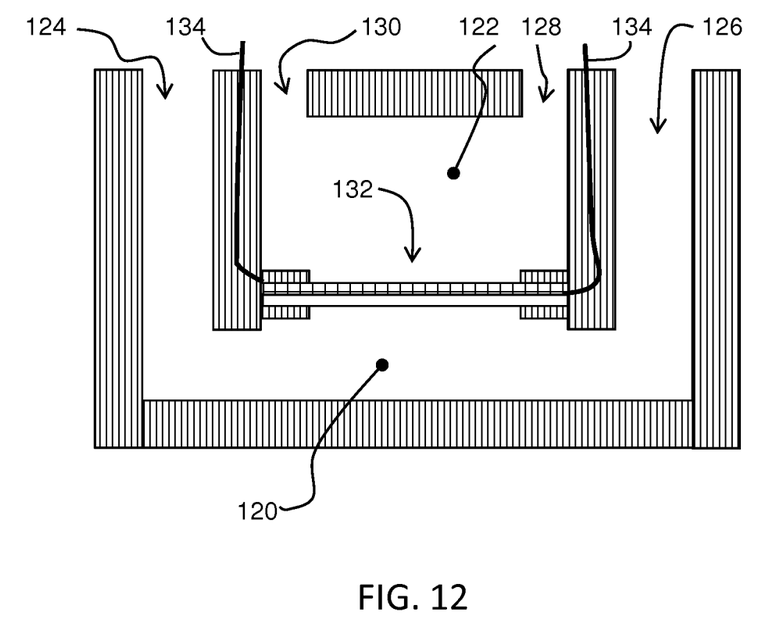
FIG. 12 shows an example of a cell culturing device.

FIG. 12 shows an example of a culturing device which is formed from two chambers 120, 122. The first chamber 120 has an inlet 124 and an outlet 126 and the second 122 has an inlet 128 and an outlet 130. The flow control device described above forms an interface 132 between the two chambers which is opened when suitable cell culturing in one or both chambers has been completed. The interface 132 is supplied by a pair of electrode connection lines 134.

Depending on the type of electroactive material, the stroke (expansion or shrinkage) can be significantly different.

Relaxor type electroactive polymers are most accurately controlled, for which around 6% strain can be applied effectively.

In the design above based on a perforated electroactive polymer layer, the electroactive material around the hole is used to open or close the holes. This implies that around 6% of the effective surface can be a hole and the rest will be the material.

An upper limit may be 10×10 mm surface area for closing one hole. The maximum hole size is then 0.6×0.6 mm. With dielectric EAP's the hole area can be much larger (as the expansion is also much larger) but they are less accurate.

In practice, more holes will be applied such as 36 holes each of 0.01 $mm^2$ per $cm^2$ of membrane.

The control accuracy is among others determined by the accuracy of the electroactive material actuator. Hysteresis effects influence the accuracy but electrical resetting functions can address this issue.

In general, a precision between 1 and 10% may be expected, depending on quality of the electroactive material and is expected to move towards 1% in the coming years.

There are a number of measures that can be taken to improve accuracy:
  the end position can be fixed mechanically;
  bi-stable EAP designs can be used;
  dedicated capacitors or strain gages can be assembled on the device to measure strain and be part of a measurement and control loop.

These measures would enable accuracies below 1%.

The hole making accuracy will also influence the actuator-to-actuator performance spread. Calibration per device can reduce this spread.

Typical membrane dimensions in an organ on chip application are a thickness of around 10 micrometer. A non-actuated orifice diameter of 0-5 micrometers may be provided and an actuated orifice diameter of 15-20 micrometers.

The invention is of interest for fluid dispensing, for example chemical dispensing (control) in oral healthcare applications, lotion dose control in skin care applications, medicine dose control for example in an electronic pill or a lab on a chip.

It may also be used for small volume chemical/biological dose control for example for mixing chemicals in cartridges or DNA building apparatus.

It may be used as a gas or fluid valve for example for PVD equipment.

The invention may also be used to provide periodic sampling for a sensor.

Materials suitable for the EAP layer are known. Electroactive polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Ionic devices may be based on ionic polymer-metal composites (IPMCs) or conjugated polymers. An ionic polymer-metal composite (IPMC) is a synthetic composite nanomaterial that displays artificial muscle behavior under an applied voltage or electric field.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

In all of these examples, additional passive layers may be provided for influencing the electrical and/or mechanical behavior of the EAP layer in response to an applied electric field.

The EAP layer of each unit may be sandwiched between electrodes. The electrodes may be stretchable so that they follow the deformation of the EAP material layer. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metallized polyester films may also be used, such as metallized polyethylene terephthalate (PET), for example using an aluminum coating.

The invention may be applied to medical and non-medical fields, for example for any small scale fluid or gas control components (valves, tubes, pumps).

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:
1. A flow control device comprising:
a laminate structure, the laminate structure comprising an electroactive material layer and a non-actuatable layer, wherein the electroactive material layer has a rest state and an actuated state wherein the electroactive material layer comprises comprising a planar layer when in one of the actuated state and rest state with opposing parallel surfaces wherein the non-actuatable layer is disposed being provided on one of the opposing parallel surfaces;

wherein the electroactive material layer comprises an array of orifices wherein the orifices are open in one of the rest state and actuated state and the orifices are closed in the other of the rest state and actuated state;

an electrode arrangement, wherein the electrode arrangement comprises two solid state electrodes in contact with the electroactive material layer, wherein each of the two solid state electrodes are disposed on each of the opposing parallel surfaces, wherein the two solid state electrodes are arranged to drive the electroactive material layer between the rest state and the actuated state a controller circuit arranged to control actuation of the electroactive material layer, wherein the non-actuatable layer comprises an array of stiffening elements, and wherein the array of stiffening elements is disposed over the electroactive material layer at locations between the orifices.

2. The device as claimed in claim 1, wherein the orifices are closed in the rest state.

3. The device as claimed in claim 1, further comprising a sealing layer, wherein the sealing layer is disposed at least around the internal openings of the orifices.

4. The device as claimed in claim 1, further comprising a breakable outer protection layer, wherein the breakable outer protection layer which is arranged to be broken by first actuation of the device.

5. The device as claimed in claim 1, wherein the electroactive material layer is arranged to expand in plane.

6. A medicine delivery system comprising:
a reservoir of medicine;
a flow control device as claimed in claim 1;
a fluid connection between the reservoir of medicine and the flow control device.

7. The system as claimed in claim 6,
wherein the flow control device comprises a chamber,
wherein the chamber has having a first face formed by the flow control device and a second face formed by a second electroactive material actuator,
wherein the second electroactive material actuator provides a pumping function.

8. The system as claimed in claim 6, wherein the flow control device comprises a chamber, wherein the chamber has having a first face formed by the flow control device,
wherein the electroactive material layer is arranged to bend when actuated, wherein the bend provides a pumping function.

9. A fluid reaction or mixing system comprising:
a set of reservoirs of different fluids;
a respective flow control device as claimed in claim 1 at a fluid output of each reservoir; and
a shared mixing reservoir at the output of the flow control devices.

10. The system as claimed in claim 9, further comprising flow control valves at an inlet and an outlet of the shared mixing chamber.

11. A fluid analysis system comprising:
a sensing chamber
a fluid sensor mounted in the chamber; and
a flow control device as claimed in claim 1, wherein the flow control device is arranged to control the flow of fluid into the sensing chamber.

12. A fluid filtering system, comprising:
a flow control device as claimed in claim 1,
wherein the controller circuit is arranged to control the orifice size, wherein the controlled orifice size provides a tunable particle filtering function.

13. The device as claimed in claim 1, wherein the electroactive material layer is arranged to bend when actuated.

14. A flow control device comprising:
a laminate structure, the laminate structure comprising an electroactive material layer and a non-actuatable layer,
wherein the electroactive material layer has a rest state and an actuated state,
wherein the electroactive material layer comprises a planar layer when in one of the actuated state and rest state with opposing parallel surfaces,
wherein the non-actuatable layer is disposed on one of the opposing parallel surfaces;
wherein the non-actuatable layer comprises an array of orifices,
wherein the orifices are open in one of the rest state and actuated state and the orifices are closed in the other of the rest state and actuated state;
an electrode arrangement, wherein the electrode arrangement comprises two solid state electrodes in contact with the electroactive material layer,
wherein each of the two solid state electrodes are disposed on each of the opposing parallel surfaces,
wherein the two solid state electrodes are arranged to drive the electroactive material layer between the rest state and the actuated state; and
a controller circuit arranged to control actuation of the electroactive material layer,
wherein the non-actuatable layer comprises an array of stiffening elements, and
wherein the array of stiffening elements is disposed over the electroactive material layer at locations between the orifices.

15. The device as claimed in claim 1, wherein the array of orifices comprises a grid of segments, the orifices comprising spaces between the segments of the grid.

16. The device as claimed in claim 15, further comprising channels or openings in the electroactive material layer.

* * * * *